United States Patent
Soon-Shiong et al.

(10) Patent No.: US 11,623,001 B2
(45) Date of Patent: Apr. 11, 2023

(54) COMPOSITIONS AND METHODS FOR VIRAL CANCER NEOEPITOPES

(71) Applicant: NantOmics, LLC, Culver City, CA (US)

(72) Inventors: Patrick Soon-Shiong, Los Angeles, CA (US); Stephen Charles Benz, Santa Cruz, CA (US); Andrew Nguyen, San Jose, CA (US); Shahrooz Rabizadeh, Los Angeles, CA (US); Kayvan Niazi, Los Angeles, CA (US); Oleksandr Buzko, Culver City, CA (US); Jay Gardner Nelson, Culver City, CA (US)

(73) Assignee: NantOmics, LLC, Culver City, CA (US)

( * ) Notice: Subject to any disclaimer, the term of this patent is extended or adjusted under 35 U.S.C. 154(b) by 0 days.

(21) Appl. No.: 15/292,095

(22) Filed: Oct. 12, 2016

(65) Prior Publication Data

US 2017/0028044 A1    Feb. 2, 2017

Related U.S. Application Data

(60) Provisional application No. 62/240,487, filed on Oct. 12, 2015.

(51) Int. Cl.
  *A61K 39/00*   (2006.01)
  *G16B 20/00*   (2019.01)

(52) U.S. Cl.
  CPC .......... *A61K 39/0011* (2013.01); *G16B 20/00* (2019.02)

(58) Field of Classification Search
  None
  See application file for complete search history.

(56) References Cited

U.S. PATENT DOCUMENTS

| | | | |
|---|---|---|---|
| 8,298,549 B2 | 10/2012 | Balint et al. | |
| 2010/0183673 A1 | 7/2010 | Balint et al. | |
| 2011/0293637 A1 | 12/2011 | Hacohen et al. | |
| 2013/0224144 A1 | 8/2013 | Balint et al. | |
| 2016/0101170 A1* | 4/2016 | Hacohen | A61K 39/0011 424/277.1 |
| 2016/0326597 A1* | 11/2016 | Chan | C07K 16/2896 |
| 2016/0339090 A1 | 11/2016 | Hacohen et al. | |
| 2021/0386842 A1 | 12/2021 | Holst et al. | |

FOREIGN PATENT DOCUMENTS

| | | |
|---|---|---|
| CN | 102292102 A | 12/2011 |
| CN | 103608033 A | 2/2014 |
| CN | 104662171 A | 5/2015 |
| EP | 2170384 | 4/2016 |
| JP | 2013-530943 A | 8/2013 |
| KR | 10-2013-0119845 A | 11/2013 |
| WO | 2001/055393 A2 | 8/2001 |
| WO | 2009006479 A2 | 1/2009 |
| WO | 2011/128448 A1 | 10/2011 |
| WO | 2011/143656 A2 | 11/2011 |
| WO | 2014031178 A1 | 2/2014 |
| WO | 2015/095811 A2 | 6/2015 |
| WO | 2015-098511 A1 | 6/2015 |
| WO | 2015-103037 A2 | 7/2015 |
| WO | 2017066256 A2 | 4/2017 |

OTHER PUBLICATIONS

Charoentong et al. (Cancer Immunol. Immunother. (2012) vol. 61:1885-1903).*
Iqbal et al. (Nature Genetics (2012) vol. 44:226-233).*
Duan et al. (The Journal of Experimental Medicine (2014) vol. 211:2231-2248).*
Starodubova et al. (Acta Naturae (2010) vol. 2, No. 1:53-59).*
Zhang, Lixin, et al., "An adenoviral vector cancer vaccine that delivers a tumor-associated antigen/CD40-ligand fusion protein to dendritic cells," Proceedings of the National Academy of Sciences, 2003, vol. 100, No. 25, pp. 15101-15106.
Sloan, J. Mark, et al., "MHC class 1 and class II presentation of tumor antigen in retrovirally and adenovirally transduced dendritic cells," Cancer Gene Therapy (2002), vol. 9, 946-950.
ISA/KR, International Search Report and Written Opinion dated Apr. 10, 2017 for Int'l Appln No. PCT/US2016/056550, 16 pages.
Fritsch, E.F., et al., "HLA-Binding Properties of Tumor Neoepitopes in Humans," Cancer Immunology Research vol. 2: pp. 522-529; Mar. 3, 2014.
Van Rooij, N, et al., "Tumor Exome Analysis Reveals Neoantigen-Specific T-Cell Reactivity in an Ipilimumab-Responsive Melanoma," Journal of Clinical Oncology, vol. 31, No. 32, pp. e439-e442; Nov. 10, 2013.
Duan, F., et al., "Genomic and bioinformatic profiling of mutational neoepitopes reveals new rules to predict cancer immunogenicity," The Journal of Experimental Medicine, vol. 211, No. 11, pp. 2231-2248; Sep. 22, 2014.
Amalfitano, A., et al., "Production and Characterization of Improved Adenovirus Vectors with the E1, E2b, and E3 Senes Deleted," Journal of Virology, Feb. 1998, pp. 926-933.
Russell, S.J., et al., "Oncolytic Virotherapy," Nat. Biotechnol.: 30(7): pp. 1-29; Jan. 10, 2014.
Kreiter, S., et al., "Mutant MHC Class II Epitopes Drive Therapeutic Immune Responses To Cancer," Nature, vol. 520, 17 pages, Apr. 30, 2015.

(Continued)

*Primary Examiner* — Lori A. Clow
(74) *Attorney, Agent, or Firm* — Martin Fessenmaier; Umberg Zipser LLP

(57) ABSTRACT

Methods and compositions for preparation and use of recombinant viruses or other recombinant expression systems are presented in which neoepitopes are first identified in a patient- and cancer-specific manner and then further filtered by HLA-match to the patient. Selected neoepitopes are then expression using sequence elements that direct the expressed neoepitope to the HLA-type (MHC-I and/or MHC-II subtype) that has desirable affinity to the filtered neoepitope.

14 Claims, 2 Drawing Sheets

(56) References Cited

OTHER PUBLICATIONS

Kreiter, S., et al., "Targeting The Tumor Mutanome For Personalized Vaccination Therapy," Oncolmmunology, vol. 1, No. 5, pp. 768-769, Aug. 2012.
Boegel, S., et al., "A Catalog of HLA Type, HLA Expression, and Neo-Epitope Candidates In Human Cancer Cell Lines," Oncolmmunology, vol. 3, No. 8, 12 pages, Aug. 1, 2014.
Larson, C., et al., "Going Viral: A Review of Replication-Selective Oncolytic Adenoviruses," Oncotarget, vol. 6, No. 24, pp. 19976-19989, Aug. 7, 2015.
Office Action received for Japanese Patent Application Serial No. 2018518962 dated Nov. 5, 2019, 12 pages.
Lee et al., "In-situ diversification of immunity following vaccination targeting tumor neoepitopes; an integral component of combinational immunotherapy", Cancer Immunology Research, May 2019, pp. 1-47.
Examination Report No. 1 received for Australian Patent Application Serial No. 2020200208 dated Jan. 21, 2021, 5 pages.
Matsushita et al., "Cancer exome analysis reveals a T-cell-dependent mechanism of cancer immunoediting", Nature, vol. 482, Feb. 16, 2012, pp. 400-406.
Carreno et al., "A dendritic cell vaccine increases the breadth and diversity of melanoma neoantigen-specific T cells", Science, vol. 348, No. 6236, Apr. 2, 2015, pp. 1-9.
Notice of Acceptance received for Australian Patent Application Serial No. 2020200208 dated Feb. 12, 2021, 5 pages.
First Office Action received for Chinese Patent Application Serial No. 201680068151.8 dated Apr. 9, 2021, 18 pages. (Including English Translation).
Office Action received for Canadian Patent Application Serial No. 3,003,302 dated May 6, 2021, 6 pages.
Office Action received for Israel Patent Application Serial No. 258688 dated Aug. 25, 2021, 9 pages. (Including English Translation).
Second Office Action received for Chinese Patent Application Serial No. 201680068151.8 dated Sep. 22, 2021, 24 pages. (Including English Translation).
Third Office Action received for Chinese Patent Application Serial No. 201680068151.8 dated Jan. 14, 2022, 35 pages. (Including English Translation).
Office Action received for Chinese Patent Application Serial No. 201680068151.8 dated Apr. 15, 2022, 43 pages. (Including English Translation).
Notice of Allowance received for Israel Patent Application Serial No. 258688 dated Jul. 27, 2022, 4 pages. (Including English Translation).
Request for the Submission of an Opinion received for Korean Patent Application Serial No. 10-2018-7013301 dated Nov. 28, 2022, 24 pages. (Including English Translation).

\* cited by examiner

COMPOSITIONS AND METHODS FOR VIRAL CANCER NEOEPITOPES

This application claims priority to U.S. provisional application with the Ser. No. 62/240,487, which was filed Oct. 12, 2015.

FIELD OF THE INVENTION

The field of the invention is genetically modified viruses as therapeutic modalities for treatment of cancer, especially as it relates to viral delivery and expression of patient specific HLA-matched neoepitopes.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

More recently, immune therapy using genetically modified viruses has become a conceptually effective and attractive route for treatment of various cancers. However, numerous challenges remain to be resolved. For example, the choice of suitable antigens to be expressed is non-trivial (see e.g., Nat Biotechnol. 2012 Jul. 10; 30(7):658-70). Moreover, even frequently expressed epitopes will not guarantee a strong and tumor-protective immune reaction in all patients. In addition, a patient will also mount an immune response against most viral vectors and as such preclude use of the virus in patients previously exposed to the virus and limit use of the vector to single use. Among other viruses, adenoviruses are commonly used for gene therapy (see e.g., Oncotarget. 2015 Aug. 21; 6(24):19976-89), but still suffer from similar drawbacks.

In an attempt to reduce immunogenicity, genetically modified adenoviruses were reported that were suitable for not only multiple vaccinations but also vaccinations in individuals with preexisting immunity to the adenovirus (see e.g., WO 2009/006479 and WO 2014/031178), typically achieved by deletion of the E2b gene and other late proteins to reduce immunogenicity. Moreover, due to these specific deletions, such genetically modified viruses were replication deficient and allowed for relatively large recombinant cargo. For example, WO 2014/031178 describes the use of such genetically modified viruses to express CEA (colorectal embryonic antigen) to provide an immune reaction against colon cancer. While at least some outcome measures improved in the treatment group using such viruses, various disadvantages nevertheless remain. Among other factors, single expressed antigens common to many tumors may not be sufficient to mount a meaningful immune response. Moreover, as immune systems vary significantly from patient to patient, predictability and efficacy for single antigens is typically not readily apparent.

Therefore, even though various systems and methods of immunotherapy for various cancers are known in the art, all or almost all of them suffer from several drawbacks. Most notably, in view of the relatively large number of neoepitopes in many cancers, parameters for neoepitopes that would predict immunogenicity have remained elusive. As such, currently known systems and methods fail to provide a rational-design approach for neoepitope-based immunotherapeutics. Consequently, there is still a need for improved systems and methods for neoepitope selection and neoepitope-based therapy creation.

SUMMARY OF THE INVENTION

The inventive subject matter is directed to systems, compositions, and methods of immunotherapy in which a rational-design approach is used to identify neoepitopes with high specificity and reactivity with respect to the patient in which the neoepitopes were identified. Such high-confidence neoepitopes are then delivered, preferably via a genetically engineered replication deficient non-immunogenic virus (i.e., will not elicit protective immunity against the virus in a host after exposure of the host to the virus) or other expression system to so stimulate an immune response.

In one aspect of the inventive subject matter, the inventors contemplate a method of treating a cancer in a patient using immunotherapy that includes a step of generating a recombinant nucleic acid configured to express a cancer- and patient-specific neoepitope. Most typically, the neoepitope is a high-affinity binder to at least one MHC Class I sub-type or at least one MHC Class II sub-type of an HLA-type of the patient. Moreover, it is contemplated that the recombinant nucleic acid in such methods comprises a sequence element that directs the expressed neoepitope toward presentation by the at least one MHC Class I sub-type or by at least one MHC Class II sub-type. In yet another step, a cell is transfected with the recombinant nucleic acid (e.g., using a virus, viral expression vector, bacterial expression vector, yeast expression vector, or RNA) to thereby force the cell to express and present the cancer- and patient-specific neoepitope on the at least one MHC Class I sub-type or on the at least one MHC Class II sub-type of the cell, wherein the step of transfecting is performed in the patient or wherein the transfected cell is administered to the patient.

It is further generally contemplated that the cancer- and patient-specific neoepitope is identified by comparing omics data from diseased tissue and healthy tissue of a patient, and/or that the cancer- and patient-specific neoepitope is identified by filtering by at least one of mutation type, transcription strength, translation strength, and a priori known molecular variations. Most typically, the high-affinity binder has an affinity to the at least one MHC Class I sub-type or the at least one MHC Class II sub-type of less than 150 nM, and/or the HLA-type of the patient is determined in silico using a de Bruijn graph.

In further aspects of such methods, the sequence element is a lysosomal targeting sequence, an endosomal targeting sequence, a peroxisomal targeting sequence, or a cytoplasmic retention sequence, and the recombinant nucleic acid may further comprise a sequence encoding a co-stimulatory molecule and/or a sequence encoding a checkpoint inhibitor.

While not limiting to the inventive subject matter, the cell are typically an immune competent cell or an antigen presenting cell of the patient, and transfection may be effected in the patient using an adenovirus. Moreover, it is contemplated that such methods may include an additional step of verifying, in a proxy cell (e.g., patient cell previously obtained from the patient or a HLA-compatible allogenic cell), presentation of the neoepitope by the at least one MHC Class I sub-type or by at least one MHC Class II sub-type. Alternatively, contemplated methods may further include a step of verifying, in a patient cancer cell or patient cancer tissue, presentation of the neoepitope by the at least one MHC Class I sub-type or by at least one MHC Class II sub-type. For example, such step of verifying may be performed using a synthetic binder or antibody that binds to the neoepitope.

In another aspect of the inventive subject matter, the inventors contemplate a method of generating a recombinant nucleic acid for immunotherapy that includes a step of comparing omics data from diseased tissue and healthy tissue of a patient to identify a disease-related patient-specific neoepitope of the patient. In another step, at least one MHC Class I sub-type and at least one MHC Class II sub-type of an HLA-type of the patient are identified, and binding affinity of the neoepitope to the at least one MHC Class I sub-type and the at least one MHC Class II sub-type is determined. The neoepitope is then selected for further use when the binding affinity is below a predetermined threshold value. In still another step of such methods, a recombinant nucleic acid (e.g., adenoviral expression vector) is constructed to include a nucleic acid sequence encoding the selected neoepitope, wherein the nucleic acid sequence encoding the selected neoepitope is under control of a promoter that drives expression of the selected neoepitope. Most typically, the nucleic acid sequence further comprises a sequence element that directs the expressed selected neoepitope toward presentation by the at least one MHC Class I sub-type or by the at least one MHC Class II sub-type.

It is generally contemplated that in such methods the step of comparing omics data is performed by incremental synchronous alignment of the omics data, and/or that the at least one MHC Class I sub-type and the at least one MHC Class II sub-type is determined in silico using a de Bruijn graph. Moreover, it is contemplated that the binding affinity of the neoepitope to the at least one MHC Class I sub-type and the at least one MHC Class II sub-type is determined in silico, wherein the predetermined threshold value is less than 150 nM.

It is further generally contemplated that the recombinant nucleic acid may further comprise a second nucleic acid sequence encoding a second neoepitope, and/or a sequence encoding a co-stimulatory molecule and/or a sequence encoding a checkpoint inhibitor. Suitable sequence elements include lysosomal targeting sequences, endosomal targeting sequences, peroxisomal targeting sequences, and/or cytoplasmic retention sequences.

Therefore, the inventors also contemplate a method of improving cancer neoantigen presentation that includes a step of comparing omics data from diseased tissue and healthy tissue of a patient to identify a plurality of disease-related patient-specific neoepitopes of the patient. In another step, the disease-related patient-specific neoepitopes are filtered by mutation type, transcription strength, translation strength, and/or a priori known molecular variations to obtain filtered neoepitopes. In yet another step, a high-affinity binder to at least one MHC Class I sub-type and to at least one MHC Class II sub-type of an HLA-type of the patient is selected from the filtered neoepitopes, and the high-affinity binder is expressed in a patient cell or a cell with compatible HLA-type. In a still further step, presentation of the high-affinity binder by the at least one MHC Class I sub-type or by the at least one MHC Class II sub-type is verified, and upon verification of expression and presentation, the high-affinity binder is used in an immunotherapeutic modality.

Most preferably, the step of comparing omics data is performed by incremental synchronous alignment of the omics data, and wherein the diseased tissue is a cancer tissue. In further contemplated aspects, the mutation type is a missense mutation, wherein the transcription strength is measured by RNAseq, wherein the translation strength is measured by selective reaction monitoring mass spectroscopy, and wherein the a priori known molecular variations comprise at least one of single nucleotide polymorphisms, short deletion and insertion polymorphisms, microsatellite markers, short tandem repeats, heterozygous sequences, multinucleotide polymorphisms, and named variants. Moreover, it is also contemplated that the high-affinity binder has an affinity to the at least one MHC Class I sub-type or the at least one MHC Class II sub-type of less than 150 nM. Additionally, it is contemplated that the patient cell or cell with compatible HLA-type in such methods is an antigen presenting cell (e.g., dendritic cell, natural killer cell, macrophage, T-cell), and/or that the cell with compatible HLA-type has the same tissue type as the diseased tissue.

The step of verifying presentation of the high-affinity binder typically uses a step of detecting binding of the high-affinity binder on the surface of the patient cell or the cell with compatible HLA-type (e.g., via a synthetic binder or antibody that binds to the high-affinity binder). In still further contemplated aspects, the immunotherapeutic modality is a recombinant adenovirus, a viral expression vector, a bacterial expression vector, a yeast expression vector, or an RNA.

In yet another aspect of the inventive subject matter, the inventors also contemplate a method of improving cancer neoantigen presentation in which in one step omics data from diseased tissue and healthy tissue of a patient are compared to identify a plurality of disease-related patient-specific neoepitopes of the patient. In another step, the disease-related patient-specific neoepitopes are filtered by at least one of mutation type, transcription strength, translation strength, and a priori known molecular variations to obtain filtered neoepitopes, and a high-affinity binder to at least one MHC Class I sub-type and to at least one MHC Class II sub-type of an HLA-type of the patient is selected from the filtered neoepitopes. In yet another step, a synthetic binder is prepared that specifically binds to the high-affinity binder, and binding of the synthetic binder to a patient cell or tissue is detected. Upon verification of binding of the synthetic peptide, the high-affinity binder is then used in an immunotherapeutic modality.

Most preferably, the step of comparing omics data is performed by incremental synchronous alignment of the omics data, and wherein the diseased tissue is a cancer tissue. In further contemplated aspects, the mutation type is a missense mutation, wherein the transcription strength is measured by RNAseq, wherein the translation strength is measured by selective reaction monitoring mass spectroscopy, and wherein the a priori known molecular variations comprise at least one of single nucleotide polymorphisms, short deletion and insertion polymorphisms, microsatellite markers, short tandem repeats, heterozygous sequences, multinucleotide polymorphisms, and named variants. Moreover, it is also contemplated that the high-affinity binder has an affinity to the at least one MHC Class I sub-type or the at least one MHC Class II sub-type of less than 150 nM.

The synthetic binder is preferably an antibody or fragment thereof, or a peptide obtained from phage display or RNA display. Moreover, with respect to the step of detecting it is contemplated that such step will comprise optical detection of the synthetic binder on the patient cell or tissue (e.g., where the patient cell or tissue is disposed in a biopsy sample). As noted before, it suitable immunotherapeutic modalities include a recombinant adenovirus, a viral expression vector, a bacterial expression vector, a yeast expression vector, or an RNA.

Consequently, and viewed from a different perspective, the inventors also contemplate a recombinant virus that includes a nucleic acid produced by methods contemplated herein. Such virus (or other expression system) may then be included in a pharmaceutical composition for treatment of cancer.

Various objects, features, aspects and advantages of the inventive subject matter will become more apparent from the following detailed description of preferred embodiments.

DETAILED DESCRIPTION

Figure 1A:
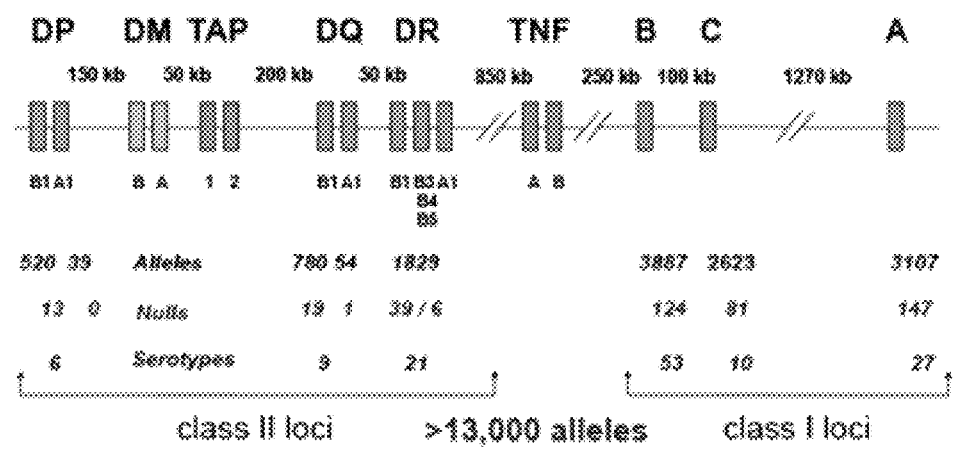
FIGS. 1A and 1B are exemplary schematic illustrations of locations of HLA-types on a human chromosome, allele diversity (FIG. 1A) and expression and membrane location (FIG. 1B).

The inventors have now discovered various systems, compositions, and methods of immunotherapy in which a viral vector or other expression system is employed to deliver one or more patient- and cancer-specific antigens to a host to produce a therapeutic effect. Most typically, the therapeutic effect is a protective immune response against cells or pathogens carrying the antigen. Therefore, and in one especially contemplated aspect of the inventive subject matter, patient- and cancer-specific neoepitopes of an individual diagnosed with cancer are determined, preferably using nucleic acid sequence information from tumor and matched normal (i.e., non-cancer) tissue samples of the patient. In this context, it should be appreciated that where neoepitopes are identified using tumor and matched normal samples, all or almost all of otherwise observed non-tumor related changes between a patient sample and a reference genome are excluded. Therefore, and viewed from a different perspective, a comparison between tumor and matched normal samples or the same patient will eliminate all interpersonal or patient-to-reference variations that occur at relatively high frequency, and as such will eliminate a large quantity of potentially false positive neoepitopes.

Additionally, to increase the likelihood of proper presentation and recognition of the so identified patient- and cancer-specific neoepitopes, the particular HLA-type of the patient is determined (e.g., using in silico prediction as described in more detail below), and binding affinity of the identified neoepitopes is tested in silico to the determined HLA-type. Most typically, the HLA-type determination includes at least three MHC-I sub-types (e.g., HLA-A, HLA-B, HLA-C) and at least three MHC-II sub-types (e.g., HLA-DP, HLA-DQ, HLA-DR), preferably with each sub-type being determined to at least 4-digit depth. Sequences for thusly identified high affinity binders are then back-translated into respective corresponding nucleic acid sequences that are then cloned into a recombinant expression system (e.g., Adenovirus Ad5 [E1-E2b-]) under the control of one or more regulatory sequences for expression in the host cell after infection with the virus. Still further, it should be appreciated that preferred expression systems will also include one or more sequence elements in connection with the neoepitope sequence(s) that will direct the expressed neoepitope(s) towards the MHC-I and/or MHC-II sub-type to which they have high affinity.

Thus, it is expected that the recombinant virus or other expression system will lead to intracellular expression of true patient- and cancer-specific neoepitopes that are not only suitable for but also directed towards HLA-presentation that was established to have a high affinity towards the neoepitope, which in turn is expected to generate an immune response with high predictability, leading to a therapeutically effective immune response against the tumor within the host.

To even further increase the chances of a therapeutically effective immune response against the tumor, the neoepitopes can be tested for expression and presentation in various manners as is further discussed in more detail below. Upon satisfactory testing in vitro, neoepitopes can then be employed as therapeutic agents in vivo, typically by expression in a cell within the patient. Of course, it should be noted that multiple neoepitopes can be used in conjunction with the teachings presented herein, and in especially preferred aspects, at least two, at least three, at least four, or at least five different neoepitopes will be employed (e.g., encoded in the same recombinant virus, or in distinct viruses). Finally, the expression system may further include additional sequences encoding proteins that support an immune response within the cellular environment where the neoepitopes are expressed. For example, suitable proteins include immune stimulatory cytokines (e.g., IL-2, IL-7, IL-12, IL-15, or a IL-15 superagonist, etc.), checkpoint inhibitors (e.g., inhibitors of CTLA-4 or PD1 signaling), and/or co-stimulatory molecules (e.g., CD80, CD86, etc.).

Choice of Neoepitopes

Neoepitopes can be characterized as expressed random mutations in tumor cells that created unique and tumor specific antigens. Therefore, viewed from a different perspective, neoepitopes may be identified by considering the type (e.g., deletion, insertion, transversion, transition, translocation) and impact of the mutation (e.g., non-sense, missense, frame shift, etc.), which may as such serve as a first content filter through which silent and other non-relevant (e.g., non-expressed) mutations are eliminated. It should further be appreciated that neoepitope sequences can be defined as sequence stretches with relatively short length (e.g., 7-11 mers) wherein such stretches will include the change(s) in the amino acid sequences. Most typically, the changed amino acid will be at or near the central amino acid position. For example, a typical neoepitope may have the structure of $A_4$-N-$A_4$, or $A_3$-N-$A_5$, or $A_2$-N-$A_7$, or $A_5$-N-$A_3$, or $A_7$-N-$A_2$, where A is a proteinogenic amino acid and N is a changed amino acid (relative to wild type or relative to matched normal). For example, neoepitope sequences as contemplated herein include sequence stretches with relatively short length (e.g., 5-30 mers, more typically 7-11 mers, or 12-25 mers) wherein such stretches include the change(s) in the amino acid sequences.

Thus, it should be appreciated that a single amino acid change may be presented in numerous neoepitope sequences that include the changed amino acid, depending on the position of the changed amino acid. Advantageously, such sequence variability allows for multiple choices of neoepitopes and so increases the number of potentially useful targets that can then be selected on the basis of one or more desirable traits (e.g., highest affinity to a patient HLA-type, highest structural stability, etc.). Most typically, neoepitopes will be calculated to have a length of between 2-50 amino acids, more typically between 5-30 amino acids, and most typically between 9-15 amino acids, with a changed amino acid preferably centrally located or otherwise situated in a manner that improves its binding to MHC. For example, where the epitope is to be presented by the MHC-I complex, a typical neoepitope length will be about 8-11 amino acids, while the typical neoepitope length for presentation via MHC-II complex will have a length of about 13-17 amino acids. As will be readily appreciated, since the position of the changed amino acid in the neoepitope may be other than central, the actual peptide sequence and with that actual topology of the neoepitope may vary considerably.

Of course, it should be appreciated that the identification or discovery of neoepitopes may start with a variety of biological materials, including fresh biopsies, frozen or otherwise preserved tissue or cell samples, circulating tumor cells, exosomes, various body fluids (and especially blood), etc. Therefore, suitable methods of omics analysis include nucleic acid sequencing, and particularly NGS methods operating on DNA (e.g., Illumina sequencing, ion torrent sequencing, 454 pyrosequencing, nanopore sequencing, etc.), RNA sequencing (e.g., RNAseq, reverse transcription based sequencing, etc.), and protein sequencing or mass spectroscopy based sequencing (e.g., SRM, MRM, CRM, etc.).

As such, and particularly for nucleic acid based sequencing, it should be particularly recognized that high-throughput genome sequencing of a tumor tissue will allow for rapid identification of neoepitopes. However, it must be appreciated that where the so obtained sequence information is compared against a standard reference, the normally occurring inter-patient variation (e.g., due to SNPs, short indels, different number of repeats, etc.) as well as heterozygosity will result in a relatively large number of potential false positive neoepitopes. Consequently, many of the identified neoepitopes will not be likely candidates for successful immunization strategies. Notably, such inaccuracies can be eliminated where a tumor sample of a patient is compared against a matched normal (i.e., non-tumor) sample of the same patient.

In one especially preferred aspect of the inventive subject matter, DNA analysis is performed by whole genome sequencing and/or exome sequencing (typically at a coverage depth of at least 10×, more typically at least 20×) of both tumor and matched normal sample. Alternatively, DNA data may also be provided from an already established sequence record (e.g., SAM, BAM, FASTA, FASTQ, or VCF file) from a prior sequence determination. Therefore, data sets may include unprocessed or processed data sets, and exemplary data sets include those having BAMBAM format, SAMBAM format, FASTQ format, or FASTA format. However, it is especially preferred that the data sets are provided in BAMBAM format or as BAMBAM diff objects (see e.g., US2012/0059670A1 and US2012/0066001A1). Moreover, it should be noted that the data sets are reflective of a tumor and a matched normal sample of the same patient to so obtain patient and tumor specific information. Thus, genetic germ line alterations not giving rise to the tumor (e.g., silent mutation, SNP, etc.) can be excluded. Of course, it should be recognized that the tumor sample may be from an initial tumor, from the tumor upon start of treatment, from a recurrent tumor or metastatic site, etc. In most cases, the matched normal sample of the patient may be blood, or non-diseased tissue from the same tissue type as the tumor.

Likewise, the computational analysis of the sequence data may be performed in numerous manners. In most preferred methods, however, analysis is performed in silico by location-guided synchronous alignment of tumor and normal samples as, for example, disclosed in US 2012/0059670A1 and US 2012/0066001A1 using BAM files and BAM servers. Such analysis advantageously reduces false positive neoepitopes and significantly reduces demands on memory and computational resources.

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

To further facilitate computational analysis and improve the treatment outcome of neoepitope based therapeutics, neoepitope sequences will be confined to relatively small fragments having a minimum size necessary for MHC-I binding (e.g., at least 5-6 amino acids) and a maximum size advantageous for MHC-I binding (e.g., 9-11 amino acids), or to relatively small fragments having a minimum size necessary for MHC-II binding (e.g., at least 12-14 amino acids) and a maximum size advantageous for MHC-II binding (e.g., 19-21 amino acids). Therefore, neoepitopes will typically have a length of between 7-12 amino acids for MHC-I binding and between 14-20 amino acids for MHC-II binding. For example, suitable neoepitopes may have a length of nine amino acids (where they are determined to bind to MHC-I), including the changed amino acid, and a length of 20 amino acids (where they are determined to bind to MHC-II), including the changed amino acid.

Viewed from a different perspective, a patient- and cancer-specific in silico collection of sequences can be established that have a predetermined length of between 5 and 25 amino acids and include at least one changed amino acid. Such collection will typically include for each changed amino acid at least two, at least three, at least four, at least five, or at least six members in which the position of the changed amino acid is not identical. Such collection can then be used for further filtering (e.g., by sub-cellular location, transcription/expression level, MHC-I and/or II affinity, etc.) as is described in more detail below.

For example, and using synchronous location guided analysis to tumor and matched normal sequence data, the inventors previously identified various cancer neoepitopes from a variety of cancers and patients, including the following cancer types: BLCA, BRCA, CESC, COAD, DLBC, GBM, HNSC, KICH, KIRC, KIRP, LAML, LGG, LIHC, LUAD, LUSC, OV, PRAD, READ, SARC, SKCM, STAD, THCA, and UCEC. All neoepitope data can be found in International application PCT/US16/29244, incorporated by reference herein.

Depending on the type and stage of the cancer, it should be noted that the number of neoepitopes may well exceed a number practical for use in immunotherapeutics. Moreover, not all of the so identified neoepitopes will necessarily lead to a therapeutically effective reaction in a patient. Indeed, it is well known in the art that only a fraction of neoepitopes will generate an immune response. To increase the likelihood of a therapeutically desirable response, the neoepitopes can be further filtered. Of course, it should be appreciated that downstream analysis need not take into account silent mutations for the purpose of the methods presented herein. However, preferred mutation analyses will provide in addition to the type of mutation (e.g., deletion, insertion, transversion, transition, translocation) also information of the impact of the mutation (e.g., non-sense, missense, etc.) and may as such serve as a first content filter through which silent mutations are eliminated. For example, neoepitopes can be selected for further consideration where the mutation is a frame-shift, non-sense, and/or missense mutation.

In a further filtering approach, neoepitopes may also be subject to detailed analysis for sub-cellular location parameters. For example, neoepitope sequences may be selected for further consideration if the neoepitopes are identified as having a membrane associated location (e.g., are located at the outside of a cell membrane of a cell) and/or if an in silico structural calculation confirms that the neoepitope is likely to be solvent exposed, or presents a structurally stable epitope (e.g., *J Exp Med* 2014), etc.

With respect to filtering neoepitopes, it is generally contemplated that neoepitopes are especially suitable for use herein where omics (or other) analysis reveals that the neoepitope is actually expressed. Identification of expression and expression level of a neoepitope can be performed in all manners known in the art and preferred methods include quantitative RNA (hnRNA or mRNA) analysis and/or quantitative proteomics analysis. Most typically, the threshold level for inclusion of neoepitopes will be an expression level of at least 20%, and more typically at least 50% of expression level of the corresponding matched normal sequence, thus ensuring that the (neo)epitope is at least potentially 'visible' to the immune system. Consequently, it is generally preferred that the omics analysis also includes an analysis of gene expression (transcriptomic analysis) to so help identify the level of expression for the gene with a mutation.

There are numerous methods of transcriptomic analysis known in the art, and all of the known methods are deemed suitable for use herein. For example, preferred materials include mRNA and primary transcripts (hnRNA), and RNA sequence information may be obtained from reverse transcribed polyA$^+$-RNA, which is in turn obtained from a tumor sample and a matched normal (healthy) sample of the same patient. Likewise, it should be noted that while polyA$^+$-RNA is typically preferred as a representation of the transcriptome, other forms of RNA (hn-RNA, non-polyadenylated RNA, siRNA, miRNA, etc.) are also deemed suitable for use herein. Preferred methods include quantitative RNA (hnRNA or mRNA) analysis and/or quantitative proteomics analysis, especially including RNAseq. In other aspects, RNA quantification and sequencing is performed using qPCR and/or rtPCR based methods, although various alternative methods (e.g., solid phase hybridization-based methods) are also deemed suitable. Viewed from another perspective, transcriptomic analysis may be suitable (alone or in combination with genomic analysis) to identify and quantify genes having a cancer- and patient-specific mutation.

Similarly, proteomics analysis can be performed in numerous manners to ascertain actual translation of the RNA of the neoepitope, and all known manners of proteomics analysis are contemplated herein. However, particularly preferred proteomics methods include antibody-based methods and mass spectroscopic methods. Moreover, it should be noted that the proteomics analysis may not only provide qualitative or quantitative information about the protein per se, but may also include protein activity data where the protein has catalytic or other functional activity. One exemplary technique for conducting proteomic assays is described in U.S. Pat. No. 7,473,532, incorporated by reference herein. Further suitable methods of identification and even quantification of protein expression include various mass spectroscopic analyses (e.g., selective reaction monitoring (SRM), multiple reaction monitoring (MRM), and consecutive reaction monitoring (CRM)).

In yet another aspect of filtering, the neoepitopes may be compared against a database that contains known human sequences (e.g., of the patient or a collection of patients) to so avoid use of a human-identical sequence. Moreover, filtering may also include removal of neoepitope sequences that are due to SNPs in the patient where the SNPs are present in both the tumor and the matched normal sequence. For example, dbSNP (The Single Nucleotide Polymorphism Database) is a free public archive for genetic variation within and across different species developed and hosted by the National Center for Biotechnology Information (NCBI) in collaboration with the National Human Genome Research Institute (NHGRI). Although the name of the database implies a collection of one class of polymorphisms only (single nucleotide polymorphisms (SNPs)), it in fact contains a relatively wide range of molecular variation: (1) SNPs, (2) short deletion and insertion polymorphisms (indels/DIPs), (3) microsatellite markers or short tandem repeats (STRs), (4) multinucleotide polymorphisms (MNPs), (5) heterozygous sequences, and (6) named variants. The dbSNP accepts apparently neutral polymorphisms, polymorphisms corresponding to known phenotypes, and regions of no variation. Using such database and other filtering options as described above, the patient and tumor specific neoepitopes may be filtered to remove those known sequences, yielding a sequence set with a plurality of neoepitope sequences having substantially reduced false positives.

In less preferred aspects, cancer- and patient-specific neoepitopes may be augmented with or even replaced by more common neoepitopes. For example, contemplated common neoepitopes include various cancer associated and cancer specific antigens (e.g., having a frequency of at least 0.1%, or at least 0.5%, or at least 1%, or at least 5%). Alternatively, suitable neoantigens may also include those identified as occurring in at least one specific MHC sub-type at a predetermined minimum frequency (e.g., having a frequency of at least 0.1%, or at least 0.5%, or at least 1%, or at least 5%). Further aspects of neoepitopes, methods, and systems related to same are disclosed in our commonly owned International applications PCT/US16/26798 and PCT/US16/29244, both incorporated by reference herein.

HLA Determination and Matching

The human major histocompatibility complex (MHC), or human leukocyte antigen (HLA) complex, comprises many genetic loci, including at least seven loci that encode two distinct classes of highly polymorphic cell surface antigens that are co-expressed. These molecules bind and present processed peptides to circulating T-cell lymphocytes and are crucial to both cellular and humoral immune responses. Consequently, in the context of immune therapeutics it should be readily apparent that neoepitopes will be more likely effective where the neoepitopes are bound to and presented by the MHC complexes.

Figure 1B:
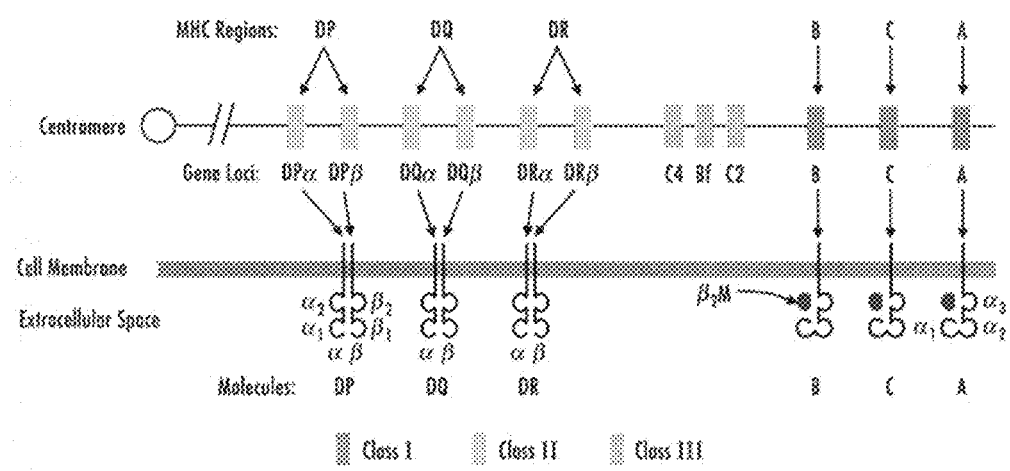

Unfortunately, however, the MHC complexes are highly diverse and distinct among different patients, rendering neoepitope binding predictions difficult. The class I molecules, HLA-A, HLA-B and HLA-C, and the class II molecules, DR, DQ and DP, are encoded in a approximately 3500 kbp segment of the short arm of chromosome 6p21.31 (schematically illustrated FIGS. 1A and 1B). Class I antigens are presented on all nucleated cells, where they act as cell surface heterodimers that primarily present peptides derived from the cytosol (viral and self peptides) to circulating CD8+ T cells. The class I cell surface heterodimer has one highly polymorphic alpha chain, with variable residues clustering within the peptide binding cleft, which is encoded by exons 2 and 3 of the gene. The HLA class I molecules also act as ligands for killer immunoglobulin receptors (KIR), which regulate the cytotoxic activity of natural killer (NK) cells. HLA class II molecules are found on the surface of B cells, macrophages and other antigen presenting cells, where the alpha-beta heterodimer presents primarily exogenously derived peptides (bacteria and chemical toxins) to circulating CD4+ T cells. In class II molecules, the beta chain contains the highly polymorphic regions, which are localized to exon 2 of the gene and encode the peptide-binding cleft.

Consequently, it should be appreciated that effective binding and presentation is a combined function of the sequence of the neoepitope and the particular HLA-type of a patient. Most typically, the HLA-type determination includes at least three MHC-I sub-types (e.g., HLA-A, HLA-B, HLA-C) and at least three MHC-II sub-types (e.g., HLA-DP, HLA-DQ, HLA-DR), preferably with each subtype being determined to at least 4-digit depth. However, greater depth (e.g., 6 digit, 8 digit) is also contemplated herein.

One the HLA-type of the patient is ascertained (using known chemistry or in silico determination), a structural solution for the HLA-type is calculated or obtained from a database, which is then used in a docking model in silico to determine binding affinity of the (typically filtered) neoepitope to the HLA structural solution. As will be further discussed below, suitable systems for determination of binding affinities include the NetMHC platform (see e.g., Nucleic Acids Res. 2008 Jul. 1; 36 (Web Server issue): W509-W512.). Neoepitopes with high affinity (e.g., less than 100 nM, less than 75 nM, less than 50 nM) for a previously determined HLA-type are then selected for therapy creation, along with the knowledge of the MHC-I/II subtype.

HLA determination can be performed using various methods in wet-chemistry that are well known in the art, and all of these methods are deemed suitable for use herein. However, in especially preferred methods, the HLA-type can also be predicted from omics data in silico using a reference sequence containing most or all of the known and/or common HLA-types as is shown in more detail below.

For example, in one preferred method according to the inventive subject matter, a relatively large number of patient sequence reads mapping to chromosome 6p21.3 (or any other location near/at which HLA alleles are found) is provided by a database or sequencing machine. Most typically the sequence reads will have a length of about 100-300 bases and comprise metadata, including read quality, alignment information, orientation, location, etc. For example, suitable formats include SAM, BAM, FASTA, GAR, etc. While not limiting to the inventive subject matter, it is generally preferred that the patient sequence reads provide a depth of coverage of at least 5×, more typically at least 10×, even more typically at least 20×, and most typically at least 30×.

In addition to the patient sequence reads, contemplated methods further employ one or more reference sequences that include a plurality of sequences of known and distinct HLA alleles. For example, a typical reference sequence may be a synthetic (without corresponding human or other mammalian counterpart) sequence that includes sequence segments of at least one HLA-type with multiple HLA-alleles of that HLA-type. For example, suitable reference sequences include a collection of known genomic sequences for at least 50 different alleles of HLA-A. Alternatively, or additionally, the reference sequence may also include a collection of known RNA sequences for at least 50 different alleles of HLA-A. Of course, and as further discussed in more detail below, the reference sequence is not limited to 50 alleles of HLA-A, but may have alternative composition with respect to HLA-type and number/composition of alleles. Most typically, the reference sequence will be in a computer readable format and will be provided from a database or other data storage device. For example, suitable reference sequence formats include FASTA, FASTQ, EMBL, GCG, or GenBank format, and may be directly obtained or built from data of a public data repository (e.g., IMGT, the International ImMunoGeneTics information system, or The Allele Frequency Net Database, EUROSTAM, www.allelefrequencies.net). Alternatively, the reference sequence may also be built from individual known HLA-alleles based on one or more predetermined criteria such as allele frequency, ethnic allele distribution, common or rare allele types, etc.

Using the reference sequence, the patient sequence reads can now be threaded through a de Bruijn graph to identify the alleles with the best fit. In this context, it should be noted that each individual carries two alleles for each HLA-type, and that these alleles may be very similar, or in some cases even identical. Such high degree of similarity poses a significant problem for traditional alignment schemes. The inventor has now discovered that the HLA alleles, and even very closely related alleles can be resolved using an approach in which the de Bruijn graph is constructed by decomposing a sequence read into relatively small k-mers (typically having a length of between 10-20 bases), and by implementing a weighted vote process in which each patient sequence read provides a vote ("quantitative read support") for each of the alleles on the basis of k-mers of that sequence read that match the sequence of the allele. The cumulatively highest vote for an allele then indicates the most likely predicted HLA allele. In addition, it is generally preferred that each fragment that is a match to the allele is also used to calculate the overall coverage and depth of coverage for that allele.

Scoring may further be improved or refined as needed, especially where many of the top hits are similar (e.g., where a significant portion of their score comes from a highly shared set of k-mers). For example, score refinement may include a weighting scheme in which alleles that are substantially similar (e.g., >99%, or other predetermined value) to the current top hit are removed from future consideration. Counts for k-mers used by the current top hit are then re-weighted by a factor (e.g., 0.5), and the scores for each HLA allele are recalculated by summing these weighted counts. This selection process is repeated to find a new top hit. The accuracy of the method can be even further improved using RNA sequence data that allows identification of the alleles expressed by a tumor, which may sometimes be just 1 of the 2 alleles present in the DNA. In further advantageous aspects of contemplated systems and methods, DNA or RNA, or a combination of both DNA and RNA can be processed to make HLA predictions that are highly accurate and can be derived from tumor or blood DNA or RNA. Further aspects, suitable methods and considerations for high-accuracy in silico HLA typing are described in International PCT/US16/48768, incorporated by reference herein.

Where desired, neoepitopes can be scored/ranked based on allele frequency multiplied by the transcripts per million number to get a likelihood score. This score can then be further augmented using HLA information and calculated for actual binding affinity to the patient's HLA type. For example, an exemplary ranking format may be:

>254 NM_001000.3 RPL39 Missense p. M29K
    A->T Normal: WIRMKTGNK, AF:
    0.179104477612 TPM: 1023.96 TPM_ME-
    DIAN: 7.35 LL: 183.395820869 netMHC:
    242.96 Allele: HLA-A03010 WIRKKTGNK.

Here, the file is a FASTA formatted file, and entries start with the '>' character, which just reports sample information. The next line is the neoepitope. In the sample information line contains a number used for indexing the sample (e.g., 254), the Refseq Gene ID (e.g., NM_001000.3), the HUGO common name (e.g., RPL39), the variant classification (e.g., Missense), the protein change (e.g., p.M29K), the base pair change (e.g., A->T), the normal epitope (e.g., Normal: WIRMKTGNK), allele frequency (e.g., AF: 0.179104477612), Transcripts per million for this gene (e.g., TPM: 1023.96), TPM_MEDIAN which is the median expression level of all the genes (e.g., TPM_MEDIAN: 7.35), the LL score which is just AF×TPM (e.g., LL: 183.395820896), the netMHC predicted binding value (e.g., netMHC: 242.96), and the specific HLA allele that the neoepitope binds to (e.g., Allele: HLA-A0301). The next line is then the neoepitope (e.g., WIRKKTGNK).

Once patient and tumor specific neoepitopes and HLA-type are identified, further computational analysis can be performed by docking neoepitopes to the HLA and determining best binders (e.g., lowest $K_D$, for example, less than 500 nM, or less than 250 nM, or less than 150 nM, or less than 50 nM), for example, using NetMHC. It should be appreciated that such approach will not only identify specific neoepitopes that are genuine to the patient and tumor, but also those neoepitopes that are most likely to be presented on a cell and as such most likely to elicit an immune response with therapeutic effect. Of course, it should also be appreciated that thusly identified HLA-matched neoepitopes can be biochemically validated in vitro prior to inclusion of the nucleic acid encoding the epitope as payload into the virus as is further discussed below.

Of course, it should be appreciated that matching of the patient's HLA-type to the patient- and cancer-specific neoepitope can be done using systems other than NetMHC, and suitable systems include NetMHC II, NetMHCpan, IEDB Analysis Resource (URL immuneepitope.org), RankPep, PREDEP, SVMHC, Epipredict, HLABinding, and others (see e.g., *J Immunol Methods* 2011; 374:1-4). In calculating the highest affinity, it should be noted that the collection of neoepitope sequences in which the position of the altered amino acid is moved (supra) can be used. Alternatively, or additionally, modifications to the neoepitopes may be implemented by adding N- and/or C-terminal modifications to further increase binding of the expressed neoepitope to the patient's HLA-type. Thus, neoepitopes may be native as identified or further modified to better match a particular HLA-type.

Moreover, where desired, binding of corresponding wild-type sequences (i.e., neoepitope sequence without amino acid change) can be calculated to ensure high differential affinities. For example, especially preferred high differential affinities in MHC binding between the neoepitope and its corresponding wildtype sequence are at least 2-fold, at least 5-fold, at least 10-fold, at least 100-fold, at least 500-fold, at least 1000-fold, etc.).

Figure 2:
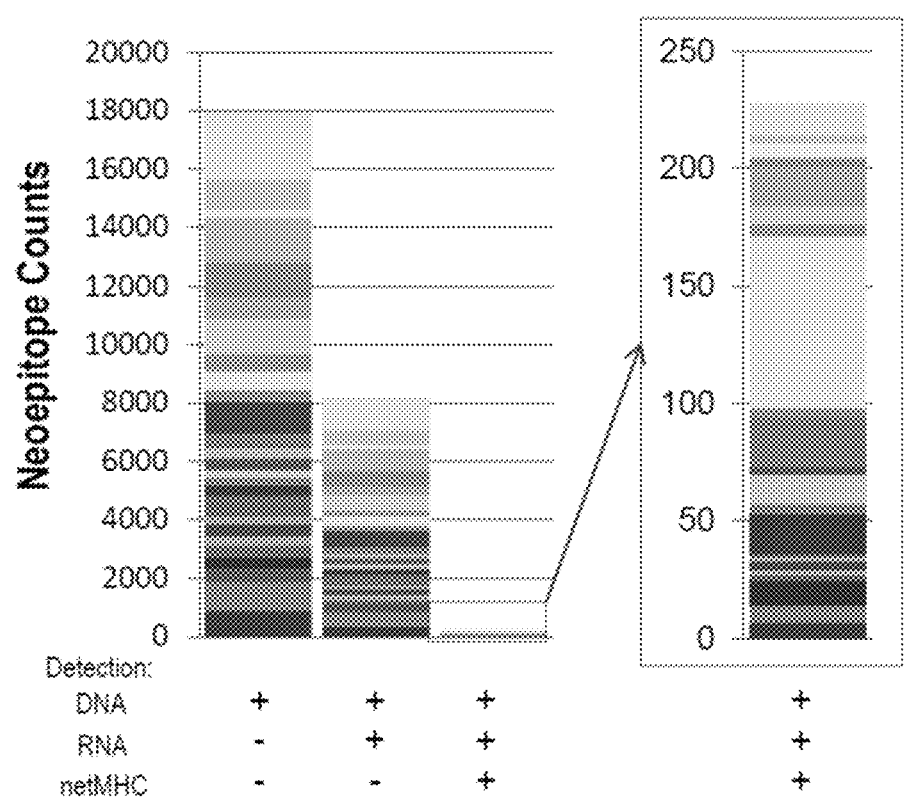
FIG. 2 is an exemplary plot depicting filtering outcomes for calculated neoepitopes.

FIG. 2 exemplarily shows a typical outcome of a series of filtering steps. Here, whole genome sequencing analysis of a triple negative breast cancer sample against matched normal (i.e., compared against non-diseased tissue of the same patient) in a synchronous location guided alignment revealed a relatively large number (~18,000) of neoepitopes in the tumor sample. Notably, a first filtering step removed more than 50% of all of the identified neoepitopes on the basis of expression strength. Here, neoepitope sequences were removed with an expression level of less than 20% of expression as compared to the matched normal sample. The remaining sequences were subjected to an in silico analysis to determine those sequences that would bind (e.g., less than 500 nM affinity) to a single specific HLA-type of the same sample. It should be noted that once more a substantial fraction of neoepitopes was eliminated, and that ultimately only less than 1.3% of all neoepitopes were found suitable for use.

It should be noted that such analysis is particularly advantageous for HLA determination from DNA and/or RNA sequencing information since each HLA-type has numerous often very similar alleles, and as traditional alignment methods typically fail to have significant differentiation capabilities where sequences have high degree of similarity. Moreover, it should be appreciated that such analysis is advantageously performed from sequencing omics data already obtained from the patient without the need for dedicated laboratory equipment. Viewed from a different perspective, neoepitope discovery, filtering, HLA-type determination, and even binding of the so identified neoepitopes to the particular HLA type of the patient can all be done in silico.

Virus Construction

Upon selection of preferred patient- and cancer-specific HLA matched neoepitopes, a recombinant nucleic acid can be constructed for intracellular expression and subsequent presentation of the neoepitopes on the cell. The recombinant nucleic acid comprises sequence portions that encode one or more patient- and cancer-specific neoepitopes in an arrangement such that the neoepitope is directed to MHC-I and/or MHC-II presentation pathways and MHC sub-type(s) for which the neoepitope is known to have high affinity. Such targeted and rational-based presentation is thought to produce a more robust immune response, which may be further augmented by subcutaneous delivery or more typically expression of one or more co-stimulatory molecules and/or checkpoint inhibitors. Of course, it should be appreciated that all manners of delivery of such recombinant nucleic acid(s) are deemed suitable and that the recombinant nucleic acid(s) may be formulated as a DNA vaccine, as a recombinant viral genome, or a DNA or RNA deliverable in a transfection composition. Therefore, it is noted that all expression systems known in the art are deemed suitable for use herein (e.g., bacterial expression systems, yeast expression systems, 'naked' DNA and RNA expression systems).

However, it is especially preferred to use viruses already established in gene therapy, including adenoviruses, adeno-associated viruses, alphaviruses, herpes viruses, lentiviruses, etc. However, among other appropriate choices, adenoviruses are particularly preferred. Moreover, it is further generally preferred that the virus is a replication deficient and non-immunogenic virus, which is typically accomplished by targeted deletion of selected viral proteins (e.g., E1, E3 proteins). Such desirable properties may be further enhanced by deleting E2b gene function, and high titers of recombinant viruses can be achieved using genetically modified human 293 cells as has been recently reported (e.g., *J Virol* 1998 February; 72(2): 926-933). Most typically, the desired nucleic acid sequences (for expression from virus infected cells) are under the control of appropriate regulatory elements well known in the art.

With respect to the integration of sequence portions that encode the neoepitopes it should be noted that the various neoepitopes may be arranged in numerous manners, and that a transcription or translation unit may have concatemeric arrangement of multiple epitopes, typically separated by short linkers (e.g., flexible linkers having between 4 and 20 amino acids), which may further include protease cleavage sites. Such concatemers may include between 1 and 20 neoepitopes (typically limited by size of recombinant nucleic acid that can be delivered via a virus), and it should be noted that the concatemers may be identical for delivery to the MHC-I and MHC-II complex, or different. Therefore, and as noted below, it should be appreciated that various peptides can be routed to specific cellular compartments to so achieve preferential or even specific presentation via MHC-I and/or MHC-II. Viewed from another perspective, it should be recognized that tumor associated antigens and neoepitopes may be presented via both presentation pathways, or selectively to one or another pathway at the same time or in subsequent rounds of treatment.

With respect to the 'payload' of the genetically modified virus it is contemplated that expression of more than one neoepitope is preferred, for example two, three, four, five, and even more, which can be accomplished using multiple distinct modified viruses, or a virus having more than one neoepitope sequence (e.g., as concatemeric or chimeric sequence). While not limiting to the inventive subject matter, it is generally preferred that neoepitope sequences are configured as a tandem minigene (e.g., $aa_{12}$-neoepitope$_{12}$-$aa_{12}$), or as single transcriptional unit, which may or may not be translated to a chimeric protein. Thus, it should be appreciated that the epitopes can be presented as monomers, multimers, individually or concatemeric, or as hybrid sequences with N- and/or C-terminal peptides. Most typically, it is preferred that the nucleic acid sequence is back-translated using suitable codon usage to accommodate the virus and/or host codon preference. However, alternate codon usage or non-matched codon usage is also deemed appropriate. With respect to further suitable configurations and expression cassettes reference is made to co-pending U.S. provisional applications with the Ser. No. 62/302,168, filed Mar. 2, 2016, and the Ser. No. 62/314,366, filed Mar. 28, 2016, incorporated by reference herein.

It should be further appreciated that neoepitope sequences (e.g., expressed as single neoepitope or as polytope) may be configured and directed to one or both MHC presentation pathways using suitable sequence elements. With respect to routing the so expressed neoepitopes to the desired MHC-system, it is noted that the MHC-I presented peptides will typically arise from the cytoplasm via proteasome processing and delivery through the endoplasmatic reticulum. Thus, expression of the epitopes intended for MHC-I presentation will generally be directed to the cytoplasm as is further discussed in more detail below. On the other hand, MHC-II presented peptides will typically arise from the endosomal and lysosomal compartment via degradation and processing by acidic proteases (e.g., legumain, cathepsin L and cathepsin S) prior to delivery to the cell membrane. Thus, expression of the epitopes intended for MHC-II presentation will generally be directed to the endosomal and lysosomal compartment as is also discussed in more detail below.

In most preferred aspects, signal peptides may be used for trafficking the neoepitopes to the endosomal and lysosomal compartment (and with directing the neoepitope presentation towards MHC-II), or for retention in the cytoplasmic space (and with directing the neoepitope presentation towards MHC-I). For example, where the peptide is to be exported to the endosomal and lysosomal compartment targeting presequences and the internal targeting peptides can be employed. The presequences of the targeting peptide are preferably added to the N-terminus and comprise between 6-136 basic and hydrophobic amino acids. In case of peroxisomal targeting, the targeting sequence may be at the C-terminus. Other signals (e.g., signal patches) may be used and include sequence elements that are separate in the peptide sequence and become functional upon proper peptide folding. In addition, protein modifications like glycosylations can induce targeting. Among other suitable targeting signals, the inventors contemplate peroxisome targeting signal 1 (PTS1), a C-terminal tripeptide, and peroxisome targeting signal 2 (PTS2), which is a nonapeptide located near the N-terminus. In addition, sorting of proteins to endosomes and lysosomes may also be mediated by signals within the cytosolic domains of the proteins, typically comprising short, linear sequences. Some signals are referred to as tyrosine-based sorting signals and conform to the NPXY or YXXø consensus motifs. Other signals known as dileucine-based signals fit [DE]XXXL[LI] or DXXLL consensus motifs. All of these signals are recognized by components of protein coats peripherally associated with the cytosolic face of membranes. YXXø and [DE]XXXL[LI] signals are recognized with characteristic fine specificity by the adaptor protein (AP) complexes AP-1, AP-2, AP-3, and AP-4, whereas DXXLL signals are recognized by another family of adaptors known as GGAs. Also FYVE domain can be added, which has been associated with vacuolar protein sorting and endosome function. In still further aspects, endosomal compartments can also be targeted using human CD1 tail sequences (see e.g., *Immunology,* 122, 522-531).

Trafficking to or retention in the cytosolic compartment may not necessarily require one or more specific sequence elements. However, in at least some aspects, N- or C-terminal cytoplasmic retention signals may be added, including a membrane-anchored protein or a membrane anchor domain of a membrane-anchored protein. For example, membrane-anchored proteins include SNAP-25, syntaxin, synaptoprevin, synaptotagmin, vesicle associated membrane proteins (VAMPs), synaptic vesicle glycoproteins (SV2), high affinity choline transporters, Neurexins, voltage-gated calcium channels, acetylcholinesterase, and NOTCH.

Additionally, it is contemplated that the viral delivery vehicle also encodes at least one, more typically at least two, eve more typically at least three, and most typically at least four co-stimulatory molecules to enhance the interaction between the infected dendritic cells and T-cells. For example, suitable co-stimulatory molecules include ICAM-1 (CD54), ICOS-L, and LFA-3 (CD58), especially in combination with B7.1 (CD80) and/or B7.2 (CD86). Further contemplated co-stimulatory molecules include 4-1BBL, CD30L, CD40, CD40L, CD48, CD70, CD112, CD155, GITRL, OX40L, and TL1A. Moreover, it should be appreciated that expression of the co-stimulatory molecules will preferably be coordinated such that the antigens and/or neoepitopes are presented along with one or more co-stimulatory molecules. Thus, it is typically contemplated that the co-stimulatory molecules are produced from a single transcript, for example, using an internal ribosome entry site or 2A sequence, or from multiple transcripts.

Likewise, it is contemplated that the viral vector will further include a sequence portion that encodes one or more peptide ligands that bind to a checkpoint receptor. Most typically, binding will inhibit or at least reduce signaling via the receptor, and particularly contemplated receptors include CTLA-4 (especially for CD8+ cells) PD-1 (especially for CD4+ cells). For example, peptide binders can include antibody fragments and especially scFv, but also small molecule peptide ligands that specifically bind to the receptors. Once more, it should be appreciated that expression of the peptide molecules will preferably be coordinated such that the antigens and/or neoepitopes are presented along with one or more peptide molecules. Thus, it is typically contemplated that the peptide molecules are produced from a single transcript, for example, using an internal ribosome entry site or 2A sequence, or from multiple transcripts.

Viruses may then be individually or in combination used as a therapeutic vaccine in a pharmaceutical composition, typically formulated as a sterile injectable composition with a virus titer of between $10^4$-$10^{11}$ virus particles per dosage unit. Alternatively, the virus may be employed to infect patient (or other HLA matched) cells ex vivo and the so infected cells are then transfused to the patient. In further examples, treatment of patients with the virus may be accompanied by allografted or autologous natural killer cells or T cells in a bare form or bearing chimeric antigen receptors expressing antibodies targeting neoepitope, neoepitopes, tumor associated antigens or the same payload as the virus. The natural killer cells, which include the patient-derived NK-92 cell line, may also express CD16 and can be coupled with an antibody. As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.).

Lastly, it should be noted that where the virus comprises a nucleic acid payload that encodes multiple neoepitopes, it is contemplated that multiple neoepitopes may at least additively or synergistically enhance the host immune response. Similarly, where multiple viruses are used with each virus having a different neoepitope, it is contemplated that multiple neoepitopes may at least additively or synergistically enhance the host immune response. Such additive or synergistic effect may be genuine to a specific tumor or stage, or specific to particular patient parameter (e.g., age, gender, previous treatment, etc.).

Testing/Quality Control

In still further contemplated approaches to identify actual expression, processing, and MHC-presentation of the neoepitopes, the inventors contemplate that the nucleic acid that encodes that neoepitope may be transfected ex vivo into in patient cells or proxy cells and that the so transfected cells may then be analyzed for MHC-presentation of the epitopes. For example, it is contemplated that such patient cells include immune competent cells, and more preferably professional antigen presenting cells (e.g., macrophages, dendritic cells, NK cells, T-cells, etc.) of the same patient. Alternatively, white blood cells (e.g., prepared by buffy coat or other manner) or partially enriched white cells may be transfected. Detection of the bound neoepitope on the surface of the cell may then be performed using antibodies or synthetic binders as described in more detail below. On the other hand, where the cells are non-patient cells, it is contemplated that these cells are HLA-matched (at least to a 4 digit level) for at least 7, or at least 8, or at least 9, or at least 10 MHC sub-types. Most preferably, such cells will be human (allogenic) cells. However, other mammalian (xenogenic) cells are also deemed suitable.

In still further contemplated aspects, verification of potential neoepitope presentation may also be performed using synthetic neoepitopes that are preferably labeled with an affinity marker or entity for optical detection. Such synthetic neoepitopes may be useful in detecting binding of the neoepitope to T-cell receptors, MHC complexes, etc. In addition, and particularly where such synthetic neoepitopes are coupled to a solid phase, the synthetic neoepitopes may be used to detect and isolate antibodies from the patient that may already be present.

To obtain a synthetic antibody against the identified neoepitope(s), it is contemplated that the in silico indentified is prepared in vitro to yield a synthetic peptide. There are numerous methods known in the art to prepare synthetic peptides, and all known manners are deemed suitable for use herein. For example, peptides with cancer neoepitope sequences can be prepared on a solid phase (e.g., using Merrified synthesis), via liquid phase synthesis, or from smaller peptide fragments. In less preferred aspects, peptides could also be produced by expression of a recombinant nucleic acid in a suitable host (especially where multiple neoepitopes are on a single peptide chain, optionally with spacers between neoepitopes or cleavage sites).

Therefore, the structure of the synthetic peptides corresponding to or comprising the neoepitope sequences may be $X$-$L_1$-$(A_n$-$L_2)_m$-$Q$, in which X is an optional coupling group or moiety that is suitable to covalently or non-covalently attaches the synthetic peptide to a solid phase, $L_1$ is an optional linker that covalently links the synthetic peptide to a solid phase or the coupling group. $A_n$ is the synthetic peptide having the neoepitope sequence with A being a natural (proteinogenic) amino acid and n is an integer between 7 and 30, and most typically between 7 and 11 or 15-25. $L_2$ is an optional linker that may be present, especially where multiple synthetic peptide sequences (identical or different) are in the construct, and m is an integer, typically between 1 and 30, and most typically between 2 and 15. Finally, Q is a terminal group which may used to couple the end of the synthetic peptide to the solid phase (e.g., to sterically constrain the peptide) or to a reporter group (e.g., fluorescence marker) or other functional moiety (e.g., affinity marker). Consequently, it should be noted that where the synthetic peptide is used for direct MHC-I binding, the overall length will be between 8 and 10 amino acids.

For example, X could be a non-covalent affinity moiety (e.g., biotin) that binds a corresponding binding agent (e.g., avidin) on the solid phase, or a chemical group (with or without spacer) that reacts with the N- or C-terminal amino or carboxyl group of the peptide, or a selectively reactive group (e.g., iodoacetyl or maleimide group) that reacts with a sulfhydryl group in the peptide or linker $L_1$. $L_1$ may be used to increase the distance of the synthetic peptide from the solid phase and will therefore typically comprise a flexible linear moiety (e.g., comprising glycol groups, alkoxy groups, glycine, etc.) having a length of equivalent to between about 2-20 carbon-carbon bonds (e.g., between 0.3 nm and 3 nm). Of course, it should also be appreciated that the synthetic peptide may use the solid phase on which the peptide was produced and as such not require a separate coupling group or linker.

Depending on the particular synthetic peptide and coupling method, it should be appreciated that the nature of the solid phase may vary considerably, and all known solid phases for attachment of peptides are deemed suitable for use herein. For example, suitable solid phases include agarose beads, polymer beads (colored or otherwise individually addressable), wall surfaces of a well in a microtiter plate, paper, nitrocellulose, glass, etc. The person of ordinary skill in the art will be readily appraised of a suitable choice of solid phase and attachment chemistry. In further preferred aspects, it is also noted that the solid phase will generally be suitable for protocols associated with phage display methods such as to allow peptides presented on a phage (or other scaffold carrier) to reversibly bind to the solid phase via the synthetic peptide. In still further contemplated uses, it should also be recognized that the solid phase may be a carrier protein used in vaccination (e.g., albumin, KLH, tetanus toxoid, diphtheria toxin, etc.), particularly where the synthetic protein is used as a vaccine in a mammal or as an immunogenic compound in a non-human mammal for antibody production. Likewise, the synthetic protein may also be used as a vaccine or immunogenic compound without any carrier.

In still further preferred methods, and as noted above, it should be recognized that where the synthetic peptide (that comprises or corresponds to the cancer neoepitope) is immobilized on a solid phase, affinity agents, and particularly antibodies, to the neoepitope may be isolated and/or refined. Most preferably, such isolation may include a prefabricated high-diversity library of antibodies. As used herein, and unless the context dictates otherwise, the term "antibody" or "antibodies" includes all isotypes and subtypes of antibodies (e.g., IgG, IgM, IgE, etc.) as well as all fragments thereof, including monovalent IgG, F(ab')$_2$, Fab', Fab, scFv, scFv-Fc, VhH, etc. Moreover, contemplated antibodies may be humanized, of human or non-human (e.g., rodent) origin, or may be chimeric. In a typical method, a high-diversity library may be a phage display library having a diversity of at least 10$^9$ diverse members, or at least 10$^{19}$ diverse members, or even higher, typically based on M13 phages and display via pIII, pVIII, pVI, or pIX, or based on T7 phages and the gene 10 capsid protein.

As should be readily appreciated, use of large diversity libraries will provide in relatively short time several binding candidate antibodies that can be further selected for best binders. Indeed, where the binding affinity to the immobilized synthetic peptide is less than desired, it should be recognized that affinity can be improved via affinity maturation using protocols well known in the art. For example, low affinity ($K_D>10^{-7}$M) binders or members of smaller libraries may be subjected to affinity maturation to improve binding affinity and/or kinetic using methods well known in the art (see e.g., *Briefings In Functional Genomics And Proteomics*. Vol 1. No 2. 189-203. July 2002). In addition, it should be noted that while antibody libraries are generally preferred, other scaffolds are also deemed suitable and include beta barrels, ribosome display, cell surface display, etc. (see e.g., *Protein Sci.* 2006 January; 15(1): 14-27), and particularly RNA display (e.g., *Proc Natl Acad Sci* 2001; 98(9):4825-6). Thus, it should be appreciated that in preferred aspects the synthetic peptide is used as a bait in a library of antibodies to so identify high-affinity binding ($K_D<10^{-7}$M, and more typically $K_D<10^{-8}$M) antibodies.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of treating a tumor in a patient using immunotherapy that targets selective patient- and tumor-specific neoepitopes, comprising:

selecting a plurality of filtered neoepitopes of the patient, wherein the filtered neoepitopes are selected by (a) comparing whole genome sequencing of a tumor sample of the patient against non-diseased tissue of the same patient to identify patient- and tumor-specific neoepitopes, followed by (b) filtering the patient- and tumor-specific neoepitopes to identify neoepitope sequences with an expression level of more than 20% of expression as compared to a matched normal sample, followed by (c) filtering from the expressed neoepitopes those that bind to the patient's HLA-type with an affinity of <500 nM and followed by (d) filtering neoepitopes that have at least 100 fold greater differential binding affinity to the patient's HLA type relative to the corresponding wildtype sequence;

generating a recombinant nucleic acid consisting of a promoter operably coupled to (a) a nucleic acid sequence encoding the plurality of filtered neoepitopes and (b) a nucleic acid sequence encoding an internal cell signaling peptide that directs the plurality of filtered neoepitopes towards presentation by the at least one MEW Class I sub-type molecule or by at least one MEW Class II sub-type molecule; and treating the tumor in the patient by administering a plurality of cells transfected with the recombinant nucleic acid.

2. The method of claim 1 wherein the step of comparing whole genome sequencing data is performed by incremental synchronous alignment of the omics data.

3. The method of claim 1 wherein the recombinant nucleic acid is a viral expression vector, a bacterial expression vector, a yeast expression vector, or an RNA.

4. The method of claim 1 wherein the internal cell signaling peptide is a lysosomal targeting sequence.

5. The method of claim 1 wherein the recombinant nucleic acid further comprises at least one of a sequence encoding a co-stimulatory molecule and a sequence encoding a checkpoint inhibitor.

6. The method of claim 1 further comprising a step of verifying, in a proxy cell, presentation of the neoepitope by the at least one MHC Class I sub-type or by at least one MHC Class II sub-type.

7. The method of claim 1, wherein the plurality of transfected cells are cells in the patient.

8. The method of claim 1, wherein the plurality of cells are transfected ex vivo.

9. The method of claim 1 wherein the internal cell signaling peptide is an endosomal targeting sequence.

10. The method of claim 1 wherein the internal cell signaling peptide is a peroxisomal targeting sequence.

11. The method of claim 1 wherein the internal cell signaling peptide is a cytoplasmic retention sequence.

12. The method of claim 1, wherein the filtered neoepitopes bind to the patient's HLA-type with an affinity of <50 nM.

13. The method of claim 1, wherein the neoepitopes are further filtered based on allele frequency.

14. The method of claim 13, further comprising scoring the filtered neoepitopes based on allele frequency multiplied by the transcripts per million number to get a likelihood score.

* * * * *